United States Patent [19]

Sandoz et al.

[11] Patent Number: 5,224,381

[45] Date of Patent: Jul. 6, 1993

[54] APPARATUS FOR AUTOMATICALLY AND NON-DESTRUCTIVELY DETERMINING THE CLASS OF STANDARDIZED MECHANICAL PROPERTIES OF A SAMPLE OF HYGROSCOPIC MATERIAL

[75] Inventors: Jean-Luc Sandoz, Chavannes/Renens; Alain Roulet, Lausanne, both of Switzerland

[73] Assignee: Sandes S.A., Granges/Veveyse, Switzerland

[21] Appl. No.: 720,803

[22] PCT Filed: Nov. 21, 1990

[86] PCT No.: PCT/CH90/00266

§ 371 Date: Jul. 23, 1991

§ 102(e) Date: Jul. 23, 1991

[87] PCT Pub. No.: WO91/08477

PCT Pub. Date: Jun. 13, 1991

[30] Foreign Application Priority Data

Dec. 1, 1989 [CH] Switzerland .................. 4317/89

[51] Int. Cl.⁵ .............................. G01N 29/18
[52] U.S. Cl. .............................. 73/597; 73/73
[58] Field of Search ............ 73/73, 335.05, 335.11, 73/335.13, 597, 618

[56] References Cited

U.S. PATENT DOCUMENTS

| | | | |
|---|---|---|---|
| 2,740,032 | 3/1956 | Bouyoucos | 73/73 |
| 2,959,959 | 11/1960 | Wellcowitz | 73/597 |
| 3,844,163 | 10/1974 | Di Leo | 73/597 |
| 3,979,581 | 9/1976 | Receland | 73/73 |
| 4,201,093 | 6/1980 | Logan | . |
| 4,413,518 | 11/1983 | Jones | . |
| 4,876,889 | 10/1989 | Shakkottai et al. | 73/597 |

FOREIGN PATENT DOCUMENTS

| | | | |
|---|---|---|---|
| 2919541 | 12/1979 | Fed. Rep. of Germany | . |
| 0145784 | 1/1962 | U.S.S.R. | 73/335.05 |
| 1632602 | 3/1971 | U.S.S.R. | 73/597 |
| 8401220 | 3/1984 | World Int. Prop. O. | . |
| 8809502 | 12/1988 | World Int. Prop. O. | . |

*Primary Examiner*—Hezron E. Williams
*Assistant Examiner*—Rose M. Finley
*Attorney, Agent, or Firm*—Ladas & Parry

[57] ABSTRACT

The apparatus of the invention has two heads each of which has three sensors for measuring the propagation speed of ultrasonic waves, the degree of moisture, and the temperature in a test material, in conjunction with a module having a microprocessor and memories. The microprocessor calculates the measured propagation speed of the ultrasonic waves. This speed is normed with respect to a set temperature (e.g., 20° C.) and a set value (e.g., 15%) of the degree of moisture. From these measurements, the microprocessor searches for the class of standardized mechanical properties in which the material falls. The microprocessor finds the class in which the value of the normed propagation speed falls in a table of values contained in one of the memories. The apparatus thereby enables the determination of the class of the material automatically and non-destructively.

9 Claims, 2 Drawing Sheets

APPARATUS FOR AUTOMATICALLY AND NON-DESTRUCTIVELY DETERMINING THE CLASS OF STANDARDIZED MECHANICAL PROPERTIES OF A SAMPLE OF HYGROSCOPIC MATERIAL

It is known that the mechanical properties of various construction materials which are hygroscopic, in particular wood, are difficult to determine, all the more so because they vary with the moisture content inside these materials.

For wood, classes (3 or 4 depending on the system) have hitherto been established experimentally and wood specialists use visual inspection to assign samples to the class which seems appropriate. This procedure is very approximate and dependent on the specialist. Furthermore, it hardly takes account of the factor of the moisture content and temperature of the material.

The aim of the present invention is to eliminate these disadvantages and to provide an apparatus for automatically and non-destructively determining the class of standardized mechanical properties of a sample of a hygroscopic material, such as wood, from measurements made by the apparatus itself on the sample in question. The invention corresponds to claim 1.

The attached drawing shows, by way of example, an embodiment of the apparatus forming the subject of the invention.

FIG. 1 shows a wooden beam 1 for which it is desired to know the class of standardized mechanical properties to which it belongs.

Two heads have been indicated very schematically by 2 and 3; each head is applied to one end of the beam 1 and, as will be seen below, has three probes or detectors for measuring the propagation time of an ultrasonic wave emitted by 2 and received by 3, the moisture content in the beam and the temperature in the beam. These detectors are of known types. 4 is a box which houses electronic devices and which is equipped with a keyboard 5 and a display 6.

Figure 2:
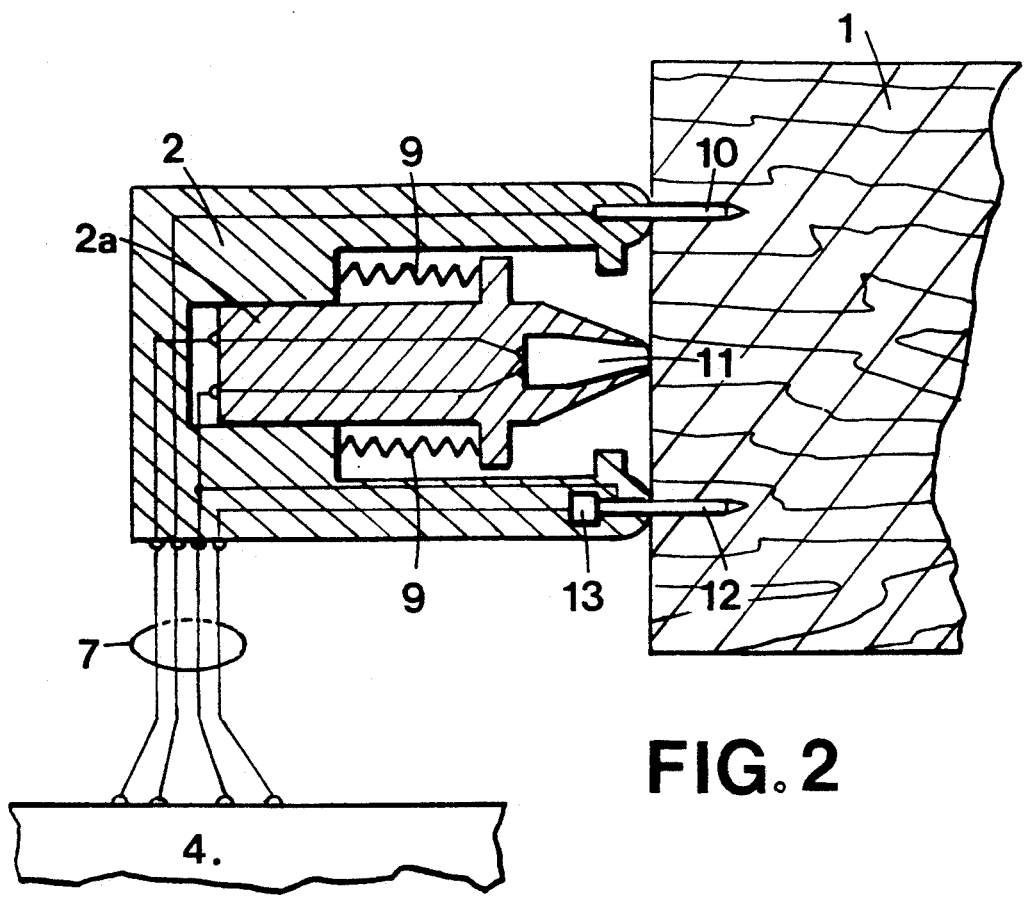
FIG. 2 is a schematic view in section of one of the two multiple detector heads belonging to this embodiment.

FIG. 2 shows the head 2. The body of the head 2 is made of an electrically insulating material. It is equipped on the inside with a sliding element 2a, inside which there is a piezoelectric transducer 11 used either for emitting or for receiving ultrasonic waves. The element 2 is firmly fixed to two metal points 10, 12 which are to be driven into the beam 1, as shown in the drawing, in order to ensure that the element 2 is fixed to one face of the beam 1 when they are driven into this face, for example by hammering the left-hand end of the head 2 in FIG. 2.

A compression spring 9 serves to apply the transducer 11 against the end of the beam. It also serves to protect the transducer from shocks when the points 10, 12 are being driven in.

These points 10, 12 act as probes for measuring the electrical resistance between them with a view to determining the moisture content inside the beam 1.

One of the points, 12, is thermally connected to a thermistor which is located in a cavity in the element 2 and which serves to measure the temperature in the beam 1. At the other end (not shown) of the beam 1, the piezoelectric transducer 11 of the element 3 receives the ultrasonic waves emitted by the transducer 11 of the element 2.

Figure 1:
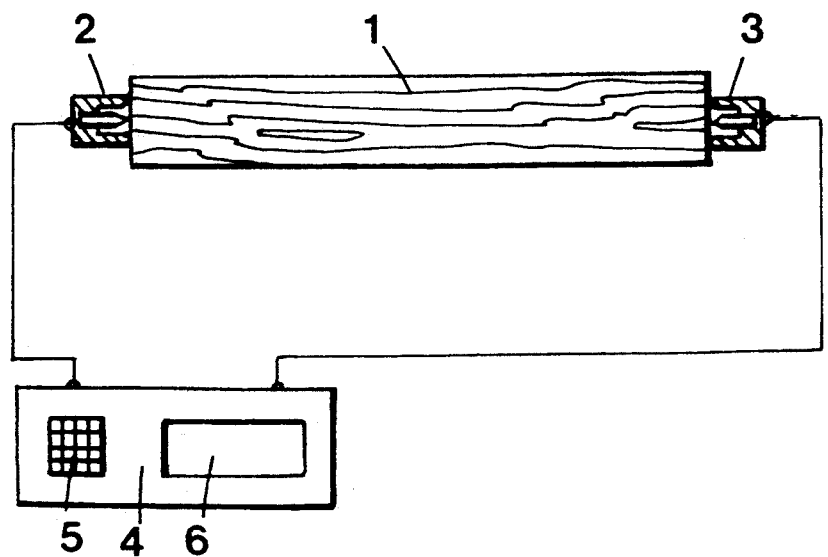
FIG. 1 is a schematic general view of this embodiment.

FIG. 1 shows that the detectors of the heads 2, 3 are electrically connected to a box 4 which houses the electronic devices indicated below, and which has a keyboard 5 and a display 6, for example of the LCD type. FIG. 2 shows that these connections are made by cables, such as 7, ensuring the transmission of the information passing from the detectors to the electronic devices which are in the box 4.

The purpose of the keyboard 5 is to provide these devices with data supplied by the operator, for example the length of the beam and a code number corresponding to the type of material (for example species of tree) of which the beam 1 is made.

In the Example according to FIG. 1, an ultrasonic wave is emitted by the device 11 of the head 2 (FIG. 2) and received by the same element of the identical head 3.

The information provided by the two devices 11, by the probes 10, 12 of the two heads 2 and 3 and by the two thermistors 13 of 2 and 3 is sent to the box 4.

Figure 3:
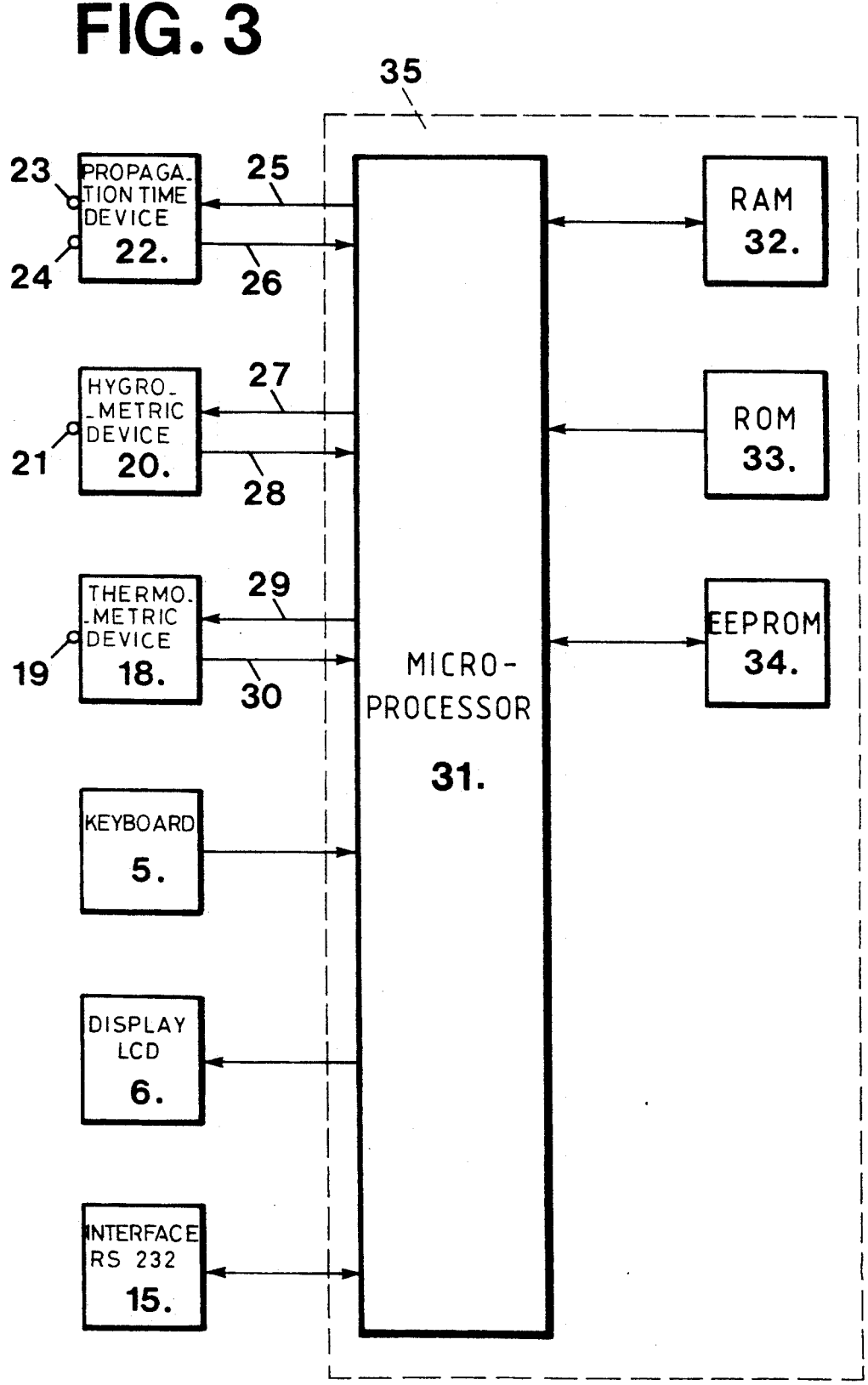
FIG. 3 is a block diagram of the apparatus according to FIG. 1.

FIG. 3 schematically shows the different electronic devices which are in the box 4 or are associated therewith.

There is a module 35 comprising a microprocessor 31 associated with a RAM 32, a ROM 33 and an EEPROM 34, the functions of which are indicated below.

There is also the following group of devices:

15: a type RS 232 series interface making it possible to establish a link with a computer (not shown), for example a PC, in order to collect the daily measurements made;

6: the LCD already mentioned;

5: the keyboard already mentioned, making it possible to enter especially the value of the length of the beam 1;

18: a thermometric device which converts the information it receives from the thermistor 13 via its terminal 19, and which provides the microprocessor, via 30, with the value of the temperature measured; the microprocessor sends operating commands to the device 18 via the line 29;

20: a hygrometric device which converts the information it receives from the hygrometric probes 10, 12 via its terminal 21 to the value corresponding to the moisture content measured, in order to send said information, via 28, to the microprocessor 31; the latter sends operating commands to the device 20 via a line 27;

22, which is joined to the piezoelectric transducers 11 of the two heads 2 and 3 by terminals 23, 24, and whose function is to determine the propagation time of the ultrasonic waves in the beam 1 and to send this value to the microprocessor 31 via the line 26; 25 is the line via which the microprocessor sends operating commands to the device 22.

The information calculated by the microprocessor, i.e. the speed of propagation of the ultrasound, the value of the moisture content measured and the temperature measured, are stored in the RAM 32. From these data, the microprocessor calculates the standardized speed of propagation of the ultrasonic wave for the standard moisture content and temperature values of 12% and 20° C., for example, according to the following procedure:

Calculation of the speed of propagation v of the ultrasonic wave:

$$v = l/t$$

l being the length of the beam and t the time taken to travel this length. The length l is entered beforehand by means of the keyboard 5 and t is measured by 22.

Calculation of the standardized speed of propagation for a standard temperature of 20° C.: The standardization coefficient $K_1$ has been determined experimentally in advance; it is stored, for each species of wood, in the ROM 33 (the code value of the species of wood of the beam 1 is entered via the keyboard 17):

$$v_{20° C.} = K_1 \cdot v$$

Calculation of the standardized moisture content according to the temperature (e.g. 20° C.). This is done from standardization tables drawn up by the manufacturer of apparatuses for measuring moisture content, for example Siemens Electronic Moisture Meters MO 5819. These tables are stored in the ROM 33. The microprocessor 31 searches these tables for the value of the moisture content at 20° C. which corresponds to the experimental value at the temperature measured by 18.

Calculation of the standardized ultrasonic speed ($v_{norm}$) for a given moisture content, for example 12% at 20° C.

The standardization coefficients $K_2$ and $K_3$ are determined experimentally in advance and the values of these coefficients are stored in the ROM 33. The value of $v_{norm}$ is $$v_{norm} = K_2 \cdot v_{20° C.} + K_3$$

The microprocessor 31 then searches a stored table of the limiting values for the propagation of ultrasonic waves in the material of which the beam 1 is made for the class corresponding to the value of this standardized ultrasonic speed.

These limiting values, which are used by the Ecole polytechnique fédérale de Lausanne, are as follows, for example, and are stored in the ROM 33:

Class 3: $v_{norm} < 5200$ m/s

Class 2: $5200$ m/s $< v_{norm} < 5400$ m/s

Class 1: $5400$ m/s $< v_{norm} < 5650$ m/s

Class 0: $v_{norm} > 5650$ m/s

When the microprocessor has found the class to which the beam 1 belongs, it indicates it on the display 6 and at the same time stores the information in the RAM 32 for subsequent use if required.

The microprocessor module 35 is equipped with a non-volatile EEPROM 34, which stores the calibration constants of the apparatus.

Although the apparatus has been described for the case of wood, it is not limited to this particular use. It can be used for any hygroscopic material for which it is desired to determine the class of mechanical properties to which it belongs.

The apparatus is of sufficiently low weight and bulk to be portable. It can be used for making measurements in any direction in the test material.

What is claimed is:

1. An apparatus for assigning a class to a sample of a hygroscopic material, said hygroscopic material being constructed and arranged such that acoustic waves can be propagated therethrough at an actual propagation velocity, said hygroscopic material having an actual temperature and an actual moisture content, the actual propagation velocity in said material varying with variations in the actual temperature and actual moisture content of the material, the material having a standardized ultrasonic velocity of propagation at a reference temperature and a reference moisture content, said material being categorizable into one of a plurality of classes according to said standardized ultrasonic velocity of propagation, said apparatus comprising:

(i) first means for propagating acoustic waves whereby they pass through the sample at said actual propagation velocity, said first means including second means for measuring the actual propagation velocity of the waves through the sample;

(ii) third means for measuring the actual moisture content in the sample; and (iii) fourth means for measuring the actual temperature in the sample;

said apparatus further comprising control means for receiving measurements of the actual temperature, actual moisture content, and actual propagation velocity from said second, third, and fourth means and for calculating therefrom the standardized ultrasonic velocity of propagation for said material at said reference temperature and reference moisture content, said control means including means for determining the class of the sample by comparing the calculated standardized ultrasonic velocity of propagation at said reference temperature and reference moisture content with standardized ultrasonic velocities of propagation for reference materials of known class at said reference temperature and reference moisture content.

2. An apparatus as claimed in claim 1, wherein the control means comprises a computer having at least four memories, a) a first of said memories containing numerical values from which can be calculated variation in velocity of acoustic waves in the material as a function of temperature;

b) a second of said memories containing numerical values from which can be calculated variation in moisture content in the material as a function of temperature;

c) a third of said memories containing numerical values from which can be calculated variation in velocity of propagation of acoustic waves in the material as a function of moisture content at the reference temperature and reference moisture content; and c) a fourth of said memories containing numerical values from which can be calculated the class of the material from the calculated standardized ultrasonic velocity of propagation for the material at said reference temperature and reference moisture content, said computer further comprising microprocessor means for receiving said measurements and for using said measurements and the numerical values in the first, second, third, and fourth memories to determine:

i) a velocity of propagation of waves in the material which is adjusted for the reference temperature;

ii) a moisture content in the material which is adjusted for the reference temperature;

iii) the standardized ultrasonic velocity of propagation in the sample at the reference temperature and reference moisture content; and
iv) the class of the sample.

3. An apparatus as claimed in claim 1, wherein the sample has a surface, the apparatus comprises at least one measuring head, said at least one measuring head having at least three detectors comprising said second, third, and fourth means, said head further comprising means for applying the head to the surface and for keeping it in contact with said surface.

4. An apparatus as claimed in claim 1, further comprising display means for displaying the class of the sample.

5. An apparatus as claimed in claim 3, wherein the first means comprises a transducer and elastic means for applying the transducer to the surface of the sample and for protecting the transducer from shocks.

6. An apparatus as claimed in claim 5, wherein the third and fourth means together comprise a plurality of probes which can be driven into the surface of the sample to keep the at least one head in contact with the sample, said probes being capable of measuring the actual moisture content in the sample by means of an electrical resistance between the respective probes, said apparatus comprising means for measuring the electrical resistance to determine the actual moisture content, said at least one head comprising a thermistor and a thermal conductor cooperating with at least one of the probes to measure the actual temperature in the sample.

7. An apparatus as claimed in claim 2, wherein the control means comprises input means by which information in numerical form can be entered into the control means manually.

8. A method for examining a sample of a hygroscopic material to assign the material to one of a plurality of classes, said hygroscopic material being constructed and arranged such that acoustic waves can be propagated through the sample of the material at an actual propagation velocity, said sample having an actual temperature and an actual moisture content, the actual propagation velocity in said sample varying with variations in the actual temperature and actual moisture content of the sample, the material having a standardized ultrasonic velocity of propagation at a reference temperature and a reference moisture content, said material being categorizable into one of a plurality of classes according to said standardized ultrasonic velocity of propagation, said method comprising the following steps:

a) propagating acoustic waves through the sample whereby the pass through the sample at said actual propagation velocity;
b) measuring the actual propagation velocity at which said waves pass through the sample, and also measuring the actual temperature and actual moisture content of the sample,
c) calculating the standardized ultrasonic velocity of propagation for said material at said reference temperature and pressure using the measurements obtained in step b; and
d) comparing the standardized ultrasonic velocity thus calculated with standardized ultrasonic velocities of propagation for reference materials of known class at said reference temperature and reference moisture content.

9. A method as claimed in claim 8, wherein the standardized ultrasonic velocity is calculated in step c according to the formula:

$$vnorm = K_2(K_1 \cdot V) + K_3$$

wherein Vnorm is the standardized ultrasonic velocity, V is the actual velocity of propagation, and $K_1$, $K_2$, and $K_3$ are standardized coefficients which are determined experimentally to provide a correlation of velocity of wave propagation through said material with temperature and moisture content of said material.

* * * * *